United States Patent
Murphy

(10) Patent No.: US 9,581,574 B2
(45) Date of Patent: Feb. 28, 2017

(54) METHOD AND DEVICE FOR DETECTING ODORANTS IN HYDROCARBON GASES

(71) Applicant: Battelle Memorial Institute, Columbus, OH (US)

(72) Inventor: Michael J. Murphy, Dublin, OH (US)

(73) Assignee: Battelle Memorial Institute, Columbus, OH (US)

( * ) Notice: Subject to any disclaimer, the term of this patent is extended or adjusted under 35 U.S.C. 154(b) by 151 days.

(21) Appl. No.: 14/563,391

(22) Filed: Dec. 8, 2014

(65) Prior Publication Data

US 2015/0160165 A1 Jun. 11, 2015

Related U.S. Application Data

(60) Provisional application No. 61/912,809, filed on Dec. 6, 2013.

(51) Int. Cl.
*G01N 29/02* (2006.01)
*G01N 33/00* (2006.01)
(Continued)

(52) U.S. Cl.
CPC ........ *G01N 33/0001* (2013.01); *G01N 29/022* (2013.01); *G01N 29/036* (2013.01);
(Continued)

(58) Field of Classification Search
CPC ............ G01N 29/022; G01N 33/0001; G01N 2291/021; G01N 26/036; G01N 29/226;
(Continued)

(56) References Cited

U.S. PATENT DOCUMENTS 3,374,659 A * 3/1968 Sanford ............... G01N 29/036
73/23.4
3,677,066 A 7/1972 King, Jr. et al.
(Continued)

FOREIGN PATENT DOCUMENTS

EP 0445927 A2 9/1991
WO 99/47905 A2 9/1999

OTHER PUBLICATIONS

Joo et al., "ZnO nanorod-coated quartz crystals as self-cleaning thiol sensors for natural gas fuel cells", Sensors and Actuators B: Chemical, 2009, vol. 138, pp. 485-490.
(Continued)

*Primary Examiner* — David Bolduc
(74) *Attorney, Agent, or Firm* — MacMillan, Sobanski & Todd, LLC

(57) ABSTRACT

A quartz crystal microbalance (QCM) is disclosed for use in a hand-held detection device for detecting the presence of an odorant in hydrocarbon gaseous fuels. The odorant is a thiol-based compound, such as ethanethiol. The QCM is coated with a coating typically containing a reagent that specifically reacts with the thiol of the odorant and alters its oscillation frequency as a result of mass gained in the reaction. Signal measurement and processing circuitry is provided for monitoring the change in oscillation frequency, for nulling out the effect of interfering compounds, and for reporting out the result.

18 Claims, 7 Drawing Sheets

(51) Int. Cl.
*G01N 29/036* (2006.01)
*G01N 29/22* (2006.01)
*G01N 29/30* (2006.01)

(52) U.S. Cl.
CPC ........... *G01N 29/226* (2013.01); *G01N 29/30* (2013.01); *G01N 33/0044* (2013.01); *G01N 2291/021* (2013.01); *G01N 2291/0255* (2013.01); *G01N 2291/0256* (2013.01); *G01N 2291/0426* (2013.01)

(58) Field of Classification Search
CPC ............... G01N 29/30; G01N 33/0044; G01N 2291/0255; G01N 2291/0426; G01N 2291/0256
See application file for complete search history.

(56) References Cited

U.S. PATENT DOCUMENTS

| | | | |
|---|---|---|---|
| 3,863,495 A * | 2/1975 | Schulz | G01N 5/04 73/61.52 |
| 3,960,494 A | 6/1976 | Verma et al. | |
| 5,996,396 A | 12/1999 | Marshall et al. | |
| 6,839,636 B1 | 1/2005 | Sunshine et al. | |
| 6,883,364 B2 | 4/2005 | Sunshine et al. | |
| 6,888,629 B1 * | 5/2005 | Boss | B82Y 15/00 356/301 |
| 7,966,132 B2 | 6/2011 | Lewis et al. | |
| 2002/0124631 A1 * | 9/2002 | Sunshine | G01N 33/0031 73/23.2 |
| 2005/0061056 A1 * | 3/2005 | Sunshine | G01N 29/022 73/23.2 |
| 2006/0191320 A1 * | 8/2006 | Pinnaduwage | G01N 29/022 73/24.06 |
| 2008/0297044 A1 * | 12/2008 | Jun | B82Y 30/00 313/504 |
| 2009/0142112 A1 * | 6/2009 | Gervasi | B41J 2/17593 399/328 |
| 2009/0289213 A1 * | 11/2009 | Pipper | B01J 20/28009 252/62.51 R |
| 2010/0231899 A1 * | 9/2010 | Hulko | C12Q 1/005 356/218 |
| 2011/0236992 A1 * | 9/2011 | Lee | B82Y 15/00 436/501 |
| 2012/0129270 A1 * | 5/2012 | Nallani | C08G 65/329 436/501 |
| 2012/0301827 A1 * | 11/2012 | Hatanaka | G03F 7/0046 430/283.1 |
| 2012/0330274 A1 * | 12/2012 | Hyde | B82Y 20/00 604/503 |
| 2015/0111765 A1 * | 4/2015 | Laury-Kleintop | G01N 29/022 506/9 |

OTHER PUBLICATIONS

PCT International Search Report and Written Opinion, Application No. PCT/US2014/069071, dated Mar. 12, 2015.

Akerfeldt et al., "Spectrophotometric Determination of Disulfides, Sulfinic Acids, Thio Ethers, and Thiols with the Palladium (II) Ion", Analytical Biochemistry, 1964, vol. 8, pp. 223-228.
Borgstrom et al., "Quantitative Determination of Mercaptans in Naphtha", Industrial and Engineering Chemistry, 1929, vol. 1, No. 4, pp. 186-187.
Cecil, "The Quantitative Reactions of Thiols and Disulphides with Silver Nitrate," Thiols and Disulphides with Silver Nitrate, 1950, vol. 47, pp. 572-584.
Cecil et al., "The Estimation of Thiols and Disulphides by Potentiometric Titration with Silver Nitrate", Estimation of Thiols and Disulphides, 1955, vol. 59, pp. 234-240.
Dunham et al., "Dual Quartz Crystal Microbalance", Analytical Chemistry, 1995, vol. 67, pp. 267-272.
Ellis et al., "Determination of Thiols in Hydrocarbon Gases", Analytical Chemistry, 1951, vol. 23, No. 21, pp. 1777-1779.
ESI, "Propane Odorant Confirmation, Independent Examiner's Report", Massachusetts Office of Attorney General, State Fire Marshal, ESI File No. 33057T, 2010, pp. 1-23.
Hankinson et al., "Vapor-Liquid Equilibrium Data for Ethyl Mercaptan in Propane Vapors", Gas Processors Association, Proceedings of Fifty-Third Annual Convention, pp. 98-100.
Hlavay et al., "Applications of the Piezoelectric Crystal Detector in Analytical Chemistry", Analytical Chemistry, 1977, vol. 49, No. 13, pp. 1890-1898.
Hongmei et al., "An Application of Artificial Neural Networks. Simultaneous Determination of the Concentration of Sulfur Dioxide and Relative Humidity with a Single Coated Piezoelectric Crystal", Analytical Chemistry, 1997, vol. 69, pp. 699-702.
Horowitz, "Chapter 5: Active Filters and Oscillators; 5.19 Quartz-crystal oscillators", The Art of Electronics, 1989, pp. 300-302.
Hussien et al., "Study the Sensitivity of Quartz Crystal Microbalance (QCM) Sensor Coated with Different Thickness of Polyaniline for Determination Vapours of Ethanol, Propanol, Hexane and Benzene", Chemistry and Materials Research, 2013, vol. 3, No. 5, pp. 61-65.
Kikuchi et al., "Quartz crystal microbalance (QCM) sensor of CH3SH gas by using polyelectrolyte-coated sol-gel film", Sensors and Actuators B, 2005, vol. 108, pp. 564-571.
Knight et al., "Measurement of Odorant Levels in Natural Gas", Industrial & Engineering Chemistry Product Research and Development, 1976, vol. 15, No. 1, pp. 59-63.
Lichter, "Crystals and Oscillators", JL9113 Rev. B, pp. 1-16.
McConnaughey, "Rapid detection method for mercaptans", Gas, 1971, vol. 47, No. 8, pp. 54-55, Abstract Only.
Schindler et al., "Determination of Mercaptan Sulfur Content of Gasolines and Naphthas: Effect of Mercuric Sulfide and Elementary Sulfur", Industrial and Engineering Chemistry, 1941, vol. 13, No. 5, pp. 326-328.
Si et al., "Polymer coated quartz crystal microbalance sensors for detection of volatile organic compounds in gas mixtures", Analytica Chimica Acta, 2007, vol. 597, pp. 223-230.
Texas Instruments, "LM2907/LM2917 Frequency to Voltage Converter", SNAS555C, Jun. 2000, pp. 1-32.
Texas Instruments, "Wide Bandwidth Precision Analog Multiplier", SBFS017A, Dec. 1995, pp. 1-8 and addendum.

* cited by examiner

METHOD AND DEVICE FOR DETECTING ODORANTS IN HYDROCARBON GASES

This application claims priority from provisional application Ser. No. 61/912,809 filed Dec. 6, 2013.

TECHNICAL FIELD

The present invention relates to the field of detecting odorants added to hydrocarbon gases and, more specifically, to a quartz crystal microbalance (QCM) device and method of using it for detecting thiol-containing odorants added to hydrocarbon gases such as propane, LPG or natural gas.

BACKGROUND OF THE INVENTION

Potentially explosive hydrocarbon fuel gases such as propane have been odorized to warn of leaks. Although the use of odorants to warn of leaks of gaseous fuels was first proposed in Germany by Von Quaglios in the 1800s, and odorants were used as early as 1900 in Europe; it was not until 1937 when a school explosion in Texas provided sufficient impetus for promulgation of U.S. laws requiring the addition of an odorant to gaseous fuels. Currently, both natural gas and propane are required to be odorized such that most people can detect the odor at ⅕ the lower flammability limit. For example, 29 CFR 1910.119 (b)(1)(i) states that "liquefied petroleum gases shall be effectively odorized by an approved agent of such character as to indicate positively, by distinct odor, the presence of gas down to concentration in air of not over one-fifth the lower limit of flammability . . . the odorization requirement of paragraph (b)(1)(i) of this section shall be considered to be met by the use of 1.0 pounds of ethyl mercaptan per 10,000 gallons of LP-gas." The requirements under 49 CFR 173.315 (b) (1) are the same.

Ethyl mercaptan, also known as ethanethiol, is the odorant of choice for 95 percent of the propane industry. However, it must be noted that although tests have shown about 9 out of 10 people can smell ethanethiol at a level of 20 ppb, this still leaves a significant number of people for whom smell is not a reliable indicator of odorant level.

An additional problem known as "odorant fade" was well documented by Beltis in "*Characterization of LP Gas Odor and Fade*," Kevin J. Beltis, Consumer Products Safety Commission report CPSC-C-86-1281, June 1986, and it may also reduce the ability to detect leaks. Odorant fade is the loss of odorant effectiveness caused by absorption, complexation and/or degradation of the odorant. For example, most odorants can be adsorbed or absorbed by materials with a high surface area, such as soil or dirt. Absorption/adsorption may also occur on the surfaces of new pipes or tanks that have not previously contained odorized propane. Moreover, odorants may be chemically oxidized to products that do not have the same degree of odor warning capability. In particular, rust in tanks is known to cause thiols (mercaptans), such as ethanethiol to oxidize to compounds of lower odor. Collectively, these absorption, adsorption, complexation and degradation phenomena are known as odor fade. Due to odor fade, there remain cases where there is doubt about the amount of odorant present in commercial propane. A recent example is the controversy about odorization levels in LP gas supplied to customers in Massachusetts and Connecticut that was reported in the March 2011 issue LP Gas Magazine.

Leakages of inadequately odorized gas present a high risk of inadvertent ignition and explosion since the ability to detect such leaks is diminished. Thus, there is a need to verify that propane fuel in fact contains the proper level of odorant. The three most common methods of testing for propane odorant are a) the "sniff" test, b) stain tubes, and c) gas chromatography. Optical methods are sometimes used in a laboratory setting. Note that odor fade can occur after delivery. Even if the propane was delivered to the supplier's tank with the proper odorant level or the propane was delivered to the customer's tank with the proper odorant level there is no certainty that the propane supplied to the customer's point of use has the proper odorant level. Testing may be needed along the entire supply chain from production to point of use.

The most basic type of test for odorant is simply a sniff test. However, it is well-known that such a test result may be subjective. There are devices that make the test semi-quantitative by diluting the sample with known quantities of air. Examples include the Heath Odorator, and the Bacharach Odorometer, developed in the 1920s. The Odorometer had drawbacks however: it required ambient air for dilution of the odor and the air had to be passed through multiple filters to remove impurities that otherwise could affect the perceived odor intensity.

Stain tubes, or length-of-stain tubes, have been used for the determination of odorant concentration. For example, Sensidyne and Draeger manufacture hermetically sealed thin glass tubes that contain a detecting reagent that produces a distinct color change when a sample of odorized propane vapor is drawn through the tube. If ethyl mercaptan is present, the detecting reagent produces a colored stain that can be measured with a calibration scale that is printed on the tube. Additionally, there is an ASTM standard for such stain tubes (Standard Test Method for Determination of Ethyl Mercaptan in Natural Gas, ASTM D5305, 2007).

Although length-of-stain tubes have a long history and enjoy ASTM Standard recognition, they have not proved fully satisfactory in the field, as the reading is somewhat subjective and the underlying accuracy is insufficient. According to ASTM Standards D1988 and D5305, the accuracy (reproducibility) of length-of-stain tubes for mercaptan measurement in gaseous fuels is plus or minus 20 to 25 percent or more. A previous Bureau of Mines study came to a similar conclusion. Moreover, visual assessment of color change is inherently subjective; some people are unable to distinguish certain colors.

At the more complex end of the analytical scale, gas chromatography can be very accurate in the laboratory, but is too expensive and awkward (bulky equipment and a compressed carrier gas supply are required) for use in the field. Similarly, Fourier transform infrared spectroscopy (FTIR) and laser-based optical absorption techniques can be sensitive, accurate, and free from interferences, but they are also complex and expensive procedures.

At least one vendor (Leister Technologies AG, Galileo-Strasse 10 CH-6056 Kaegiswil/Switzerland—See more at: http://www.leister.com/en/) offers a commercial laser diode spectrometer that could be suitable for mercaptan measurement. But this gas detector costs thousands of dollars exclusive of the power supply, sample pump, and sampling handling components.

The need for an inexpensive and portable detector that can monitor odorant concentrations along the entire supply line greatly complicates the development of an odorant meter. It means that an odorant meter cannot be a complex or expensive device that is used only at a production plant or at a supplier's headquarters. The meter must be portable and practical for field use by delivery and service personnel who are normally at the customer's premises.

These and other problems are addressed by the present invention.

SUMMARY OF THE INVENTION

In a first aspect, the invention includes a portable device for detecting thiol odorants in a hydrocarbon gas, the device comprising:

a housing;

at least one piezo-crystalline substrate disposed in the housing and located for fluid communication with the hydrocarbon gas, a coating on the piezo-crystalline substrate, the coating capable of reacting specifically with and capturing thiol components from a gaseous phase, while substantially not reacting with the hydrocarbon gas itself;

a power source;

an oscillator circuit, the piezo-crystalline substrate forming a part of the oscillator circuit, whereby, when powered by the power source, the piezo-crystalline substrate oscillates at a first frequency prior being exposed to thiol odorants in a gas, and at a second frequency after being exposed to thiol odorants in the gas and capturing thiols in the coating, the second frequency differing from the first frequency in proportion to the amount of thiol captured.

In a second major aspect, the invention comprises a method for detecting thiol odorants in a hydrocarbon gas using the hand-held portable detector of claim 1, the method comprising:

providing a piezo-crystalline substrate having a coating capable of reacting specifically with and capturing thiol components from a gaseous phase while substantially not reacting with hydrocarbons of the gas, the piezo-crystalline substrate forming a part of an oscillator circuit that oscillates at a first frequency of oscillation;

exposing the coated, piezo-crystalline substrate to a gas suspected to contain a thiol odorant for a time sufficient to allow the coating to capture thiols if present in the gas;

powering the oscillator circuit after exposure to the gas to attain a second frequency of oscillation;

determining the extent to which the second frequency differs from the first frequency as a measure of the thiol captured from the gas.

In some embodiments the piezo-crystalline substrate is a quartz crystal. In some embodiments, the crystal oscillates at between 3 and 15 MHz.

In some embodiments the coating is applied directly to the surface of the crystal; while in other embodiments a porous layer is placed between the crystal and the coating to increase the surface area of the coating. In most embodiments, the coating is oleophobic. In some embodiments, the coating includes a capture reagent specific for the thiol odorant and does not react to hydrocarbon gases.

For example, the oleophobic coating may comprise a reagent selected from the group consisting of:

(a) Bis(p-nitrophenyldisulphide) in a phosphate buffer;

(b) Mercury perchlorate with pyridine in an aqueous acetone solution;

(c) Sodium nitrate and glacial acetic acid in aqueous solution;

(d) Sodium nitroprusside in aqueous hydroxide base;

(e) Phosphomolybdic acid in aqueous NaOH; and (f) N-Ethylmaleimide in 2-alcohol

In some embodiments, the invention further comprises at least one reference piezo-crystalline substrate disposed in the housing and located for fluid communication with the hydrocarbon gas. The reference crystal may also be quartz and may be identical to the first crystal. In some cases, the reference crystal is uncoated; while in other cases the reference crystal is coated, but with no specific capture reagent or with a reagent specific for a potentially interfering substance.

Various advantages of this invention will become apparent to those skilled in the art from the following detailed description of the preferred embodiment, when read in light of the accompanying drawings.

DETAILED DESCRIPTION OF THE INVENTION

Figure 1:
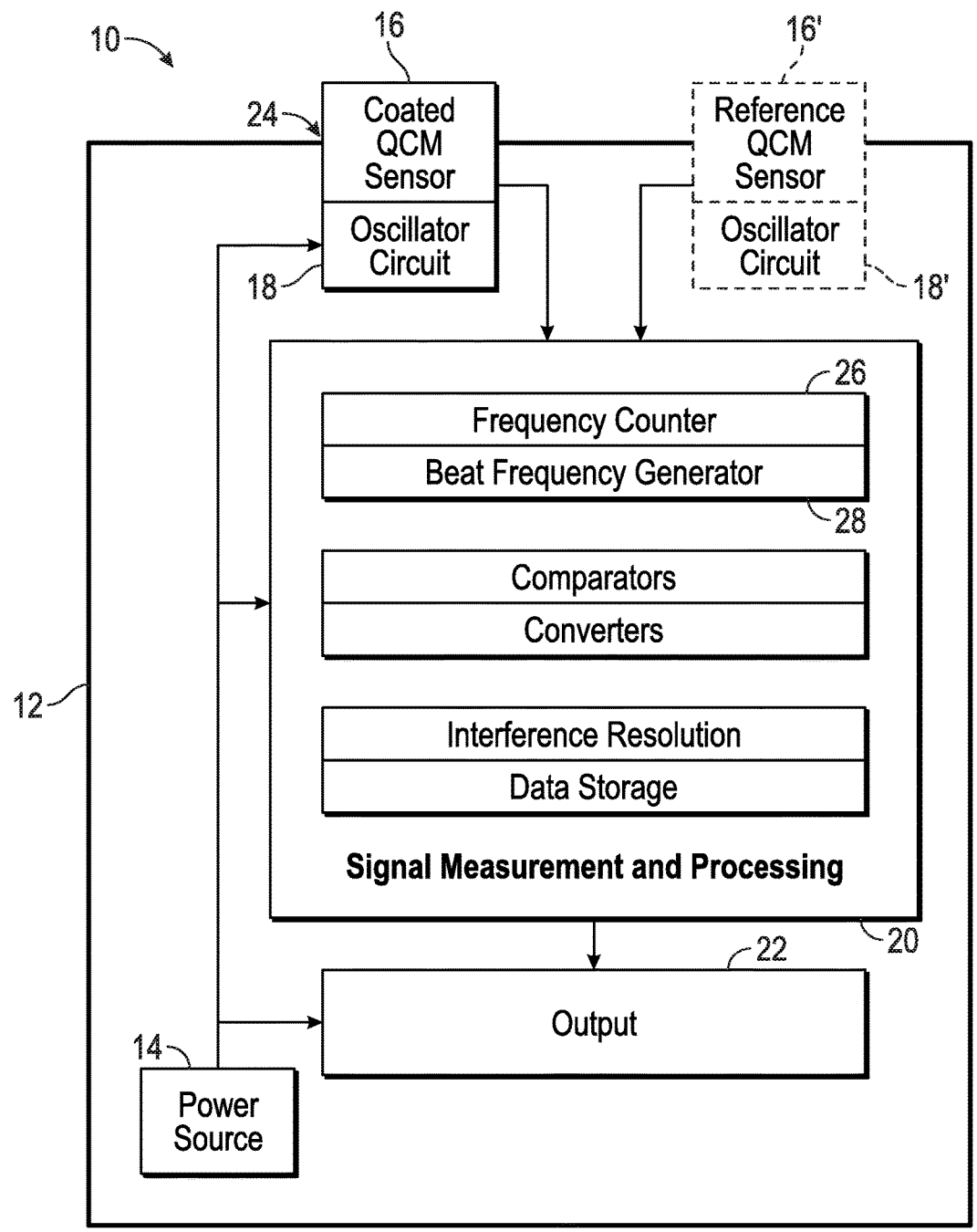
FIG. 1 is a schematic illustration of a detection device of the present invention, and shows an optional, alternate embodiment in dashed lines.

Unless defined otherwise, all technical and scientific terms used herein have the same meaning as commonly understood by one of ordinary skill in the art to which the invention belongs. All references cited herein, including books, journal articles, published U.S. or foreign patent applications, issued U.S. or foreign patents, and any other references, are each incorporated by reference in their entireties, including all data, tables, figures, and text presented in the cited references.

In the drawings, the thickness of the lines, layers, and regions may be exaggerated for clarity.

Unless otherwise indicated, all numbers expressing ranges of magnitudes, such as angular degrees, percentages, quantities of ingredients, properties such as molecular weight, reaction conditions, and so forth as used in the specification and claims are to be understood as being modified in all instances by the term "about." This is due, in large part, to the fact that numerical values inherently contain certain errors necessarily resulting from their respective measurement systems. Accordingly, unless otherwise indicated, the numerical properties set forth in the specification and claims are approximations that may vary depending on the desired properties sought to be obtained in embodiments of the present invention. All numerical ranges are understood to include all possible integral sub-ranges within the outer boundaries of the range. Thus, a range of 30 to 90 percent discloses, for example, 35 to 51 percent, 45 to 85 percent, and 43 to 80 percent, etc.

Thiol Odorants in Hydrocarbon Gases

Hydrocarbon gases, as used herein, refer to compositions consisting mainly of straight or branched hydrocarbons having from 1 to 6 carbons. They are generally gaseous at room temperature and atmospheric pressure, but under sufficiently high pressures or sufficiently low temperatures they may become liquids. Because they are frequently distilled and condensed from various sources (e.g. petroleum, coal, etc) they frequently may not be completely pure, and may be a mixture or blend of various length hydrocarbons. Examples of hydrocarbon gases include methane, ethane, propane, butane and pentane, and mixtures thereof. Hydrocarbons of 4 or more carbons may be straight or branched. Also included within "hydrocarbon gases" are natural gas (a mixture that is predominantly methane), other blends of lower hydrocarbons, and compressed or liquid forms of these, such as LPG and CNG.

Thiol odorants have the general formula R—SH, where R is a hydrocarbon chain having from 1 to 6 carbons. Odorants include, for example, methanethiol, ethanethiol, propanethiol and butanethiol. The —SH, or thiol, group is known to impart the smell characterized often as "rotting eggs." Compounds containing it are variously referred to generally as thiols or mercaptans.

For commercial propane, the requirement for an odorant is deemed to be met by the addition of 1.0 pounds of ethanethiol, also known as ethyl mercaptan, to each 10,000 gallons of liquid propane. However, it is the general custom in the industry to add 1.5 pounds of ethanethiol to each 10,000 gallons.

Ethanethiol has the chemical formula $CH_3CH_2SH$. The boiling point of ethanethiol at atmospheric pressure is 35° C. Ethanethiol is moderately soluble in water with a solubility of 6.8 grams per liter.

In general and depending on the conditions, a compound partitions between a liquid phase and an adjacent vapor phase according to its partition coefficient, K. The concentration of ethanethiol in the gas phase is thus different than that in the liquid phase, and this difference defines the so-called K ratio. Hankinson and Wilson report measured K ratio values for ethanethiol in propane ranging from 0.30 at 40° F. to 0.37 at 100° F. (See *Vapor-Liquid Equilibrium Data for Ethyl Mercaptan in Propane Vapors*, R. W. Hankinson, Grant M. Wilson, Proceedings of the Fifty-Third Annual Convention, 1974, page 98.) Thus, the 1.5 lb per 10,000 gallons treat rate amounts to about 36 ppm ethanethiol by mass in the liquid propane and, using a K ratio of 0.35, about 9 ppm ethanethiol by volume in the vapor. As used herein, "ppm" means parts per million and, as is conventional in the industry, it is expressed as a mass ratio for liquids and as a volume ratio for gasses.

Thus, the level of ethanethiol odorant in a typical propane gas may vary from about 5 ppm to about 20 ppm, more typically from about 7 ppm to about 15 ppm, and often about 8-12 ppm. K ratios and expected odorant levels for other thiol odorants in other hydrocarbon gasses may be determined empirically or estimated based on the experience with ethanethiol in propane gas.

Fitness Characteristics of Odorant Meter for Field Use

To be most useful in the field, the odorant meter should be present on each service truck; the instrument should be easily carried, weigh no more than 5 to 10 lb, and run on battery power for at least a typical day's use. It should cost no more than about $1000 per unit, preferably less than $700, preferably less than $500.

Given the variability in sensitivity of the human nose to detect odorants, an accuracy of about 10% is deemed adequate. Of course, higher accuracies of 8%, 5%, 3% or more are preferred. Perhaps more importantly, the results of the meter should be objective and reproducible regardless of who is operating the instrument. In addition, the method used to determine odorant concentration must be resistant to errors caused by impurities in the propane. These impurities include heavy ends, lubricating oils, materials leached from transfer hoses, dirt, and moisture. See, e.g. *Liquefied Petroleum Gases*, A. F. Williams and W. L. Lom, 1982.

As noted above, propane odorants are generally added so that there is somewhat less than 10 ppm of odorant in the propane vapor. A useful detector device must therefore be sensitive at the sub-10 ppm level. In order to achieve a 10 percent accuracy level, the meter must be able to distinguish odorant levels of 1 ppm.

Quartz Crystal Microbalance-Based Sensors

There is a known group of crystalline substances that experience the piezoelectric effect. The piezoelectric effect has found applications in high power sources, sensors, actuators, frequency standards, motors, etc., and the relationship between applied voltage and mechanical deformation is well known. This feature allows probing an acoustic resonance by electrical means. Quartz is the most studied and most prevalent crystal that exhibits the piezoelectric effect ("piezo-crystal") and will be used for the ensuing exemplary description of a quartz crystal microbalance (QCM)—which is but one example of a piezo-crystalline substrate that is a sensitive and cost effective solution for detection of odorants in hydrocarbon gases. Other natural and synthetic materials that exhibit piezoelectric effect include Berlinite ($AlPO_4$), a rare phosphate mineral that is structurally identical to quartz, sucrose (table sugar), Rochelle salt, Topaz, and the Tourmaline-group minerals. Most piezo-crystals exhibit frequency drift as the temperature varies.

Various crystal cuts of quartz (and of other piezo-crystals) are known and described in the literature. See, e.g. *Crystals and Oscillators*, Jerry Lichter, JL9113 Rev C. an NEL Frequency and Controls Application Note published at: http://www.nelfc.com/app_notes.html (web accessed 4 Dec. 2013, original publication date unknown); and *Recent Advances in Quartz Crystal Microbalance-Based Sensors*, Sandeep. K. Vashist and Priya Vashist, Journal of Sensors, Vol. 2011, Article ID 571405, 2011. The classification of crystal cuts as AT, BT, SC, DT, CT, and GT has to do with the method by which the waves are propagated in the crystal. AT, BT, and SC cuts propagate by thickness shear mode vibration and are preferred. DT, CT, and GT cut crystals propagate by face shear mode vibration.

For AT cut crystals, the frequency constant is 1.661 MHz-mm, and is generally limited to approximately 40 MHz on the fundamental mode for small diameter blanks. Using contouring techniques the low end of the AT frequency range is approximately 500 kHz, but is dependent on holder size. The BT cut, having a frequency constant of 2.536 MHz-mm, can extend the upper frequency range above that of the AT cut to more than 50 MHz. The BT cut is not as widely accepted as the AT cut because of its poorer temperature characteristics in most applications; however, the use of a suitable reference sensor may obviate this problem. The frequency constant for the SC cut is 1.797 MHz-mm. However, this cut is also less preferred due to the complexities introduced by the non-orthogonal axes relative to the plane of propagation.

The frequency of oscillation of the quartz crystal is partially dependent on the thickness of the crystal. During normal operation, all the other influencing variables remain constant; thus a change in thickness correlates directly to a change in frequency. As mass is deposited on the surface of the crystal, the thickness increases; consequently the frequency of oscillation decreases from the initial value. With some simplifying assumptions, this frequency change ($\Delta F$) can be quantified and correlated precisely to the mass change ($\Delta Ms$) using the Sauerbrey equation: $\Delta F/F = -\Delta Ms F/A\rho N$, where F refers to frequency (MHz), $\Delta Ms$ is the incremental mass of a substance coated on the crystal surface (g), A is the area coated ($cm^2$), $\rho$ is the density of the crystal, and N is the frequency constant. Using the density and frequency constant for AT-cut quartz crystals, and rearranging, the equation distills to: $\Delta F=-2.3\times10^6 (F^2)(\Delta Ms/A)$. See, e.g. *Applications of the Piezoelectric Crystal Detector in Analytical Chemistry*, J. Hlavay and G. G. Guilbault, Analytical Chemistry, Vol. 49, No. 13, November, 1977).

Figure 2:
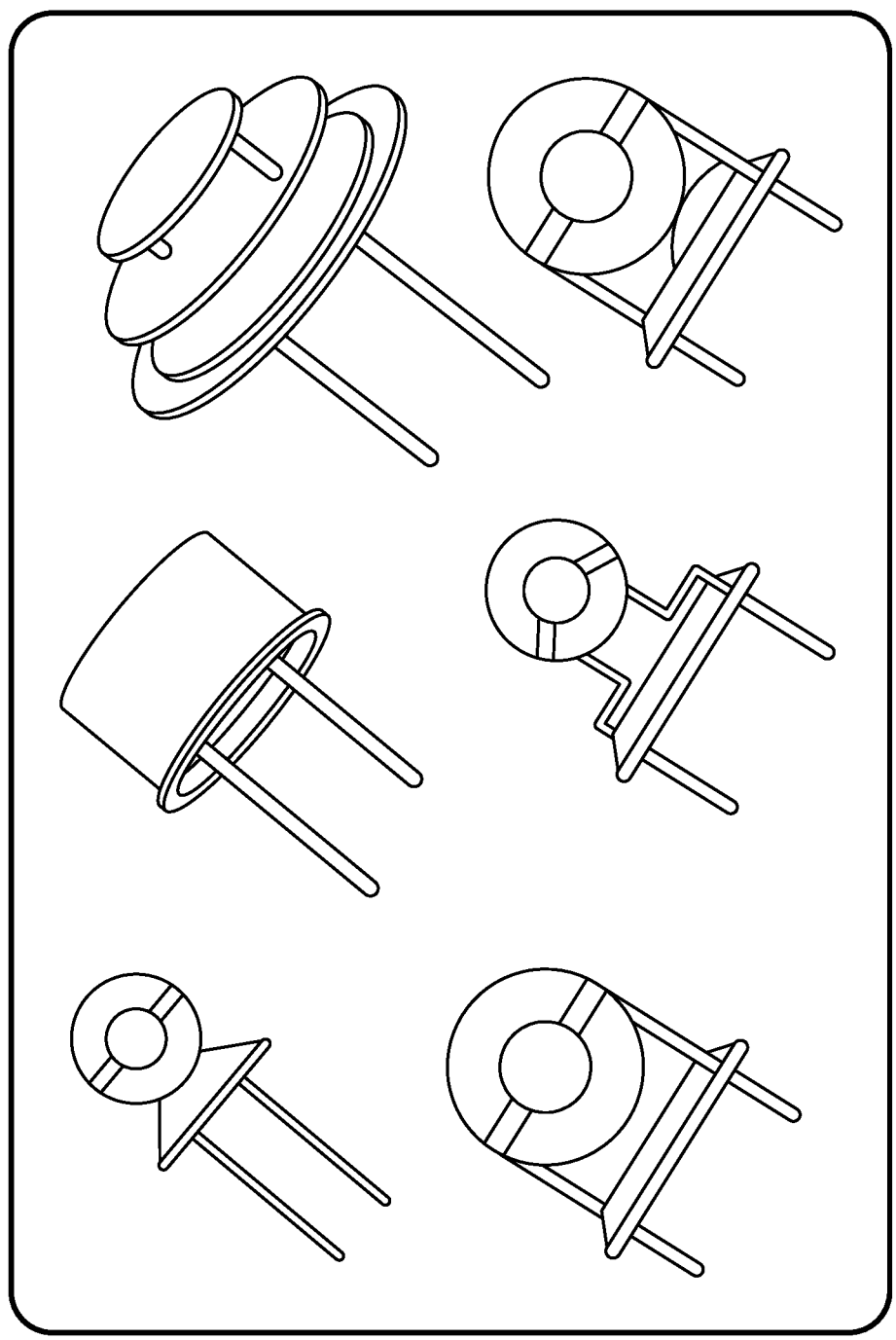
FIG. 2 is a representation of some typical QCM sensors.

FIG. 2 illustrates several QCM-based sensors, also referred to herein as QCM sensors or simply "sensors." They have electrodes or terminals for electrically connecting into circuitry (described later). QCM sensors exploit the gravimetric features of piezo-crystals, and in particular of AT cut quartz crystals, to measure very small changes in mass. The crystal is part of an oscillator circuit and the frequency of oscillation changes when the coating on the crystal is exposed to a material which reacts with the coating. Sensors based on the QCM principal use a quartz crystal that is coated with a reagent sensitive to the analyte of interest. QCM-based detectors have been made for many analytes, including ammonia, ozone, formaldehyde, toluene, water vapor, amines, nerve gases, a nerve gas stimulant, DMMP (Dimethyl Methylphosphonate), sulfur dioxide, and many others. Vashist and Vashist, have reviewed a number of QCM sensors described in the literature. See *Recent Advances in Quartz Crystal Microbalance-Based Sensors*, Sandeep. K. Vashist and Priya Vashist, Journal of Sensors, Vol. 2011, Article ID 571405, 2011.

Figure 3A:
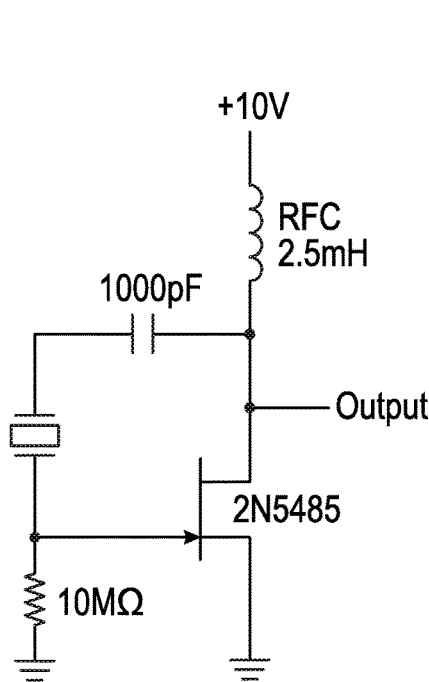
FIG. 3, in parts A through E, depict electronic circuit schematics for several types of known oscillator circuits useful with the invention.
Figure 3B:
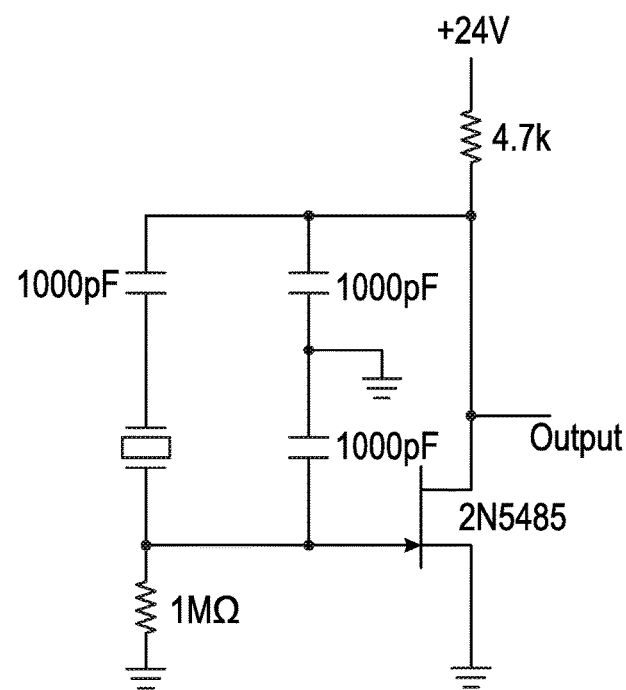
Figure 3C:
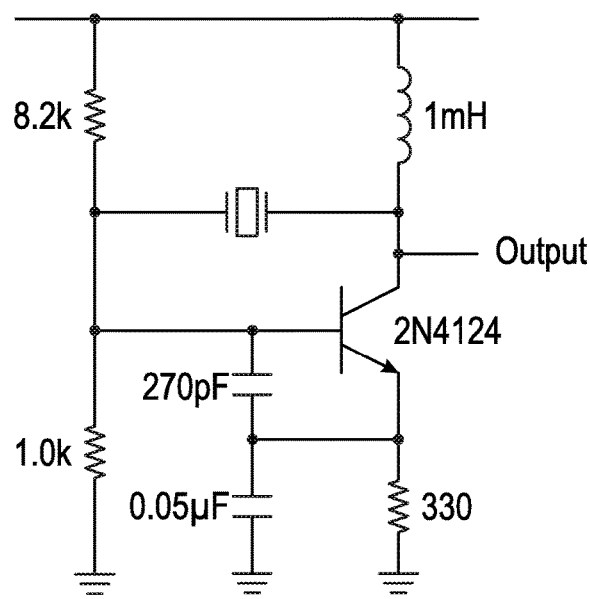
Figure 3D:
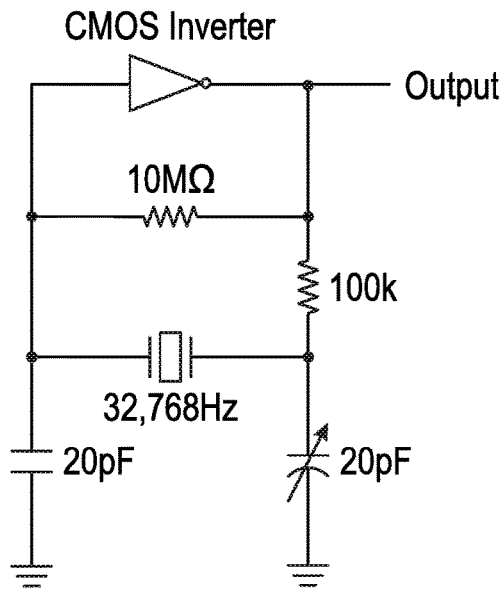
Figure 3E:
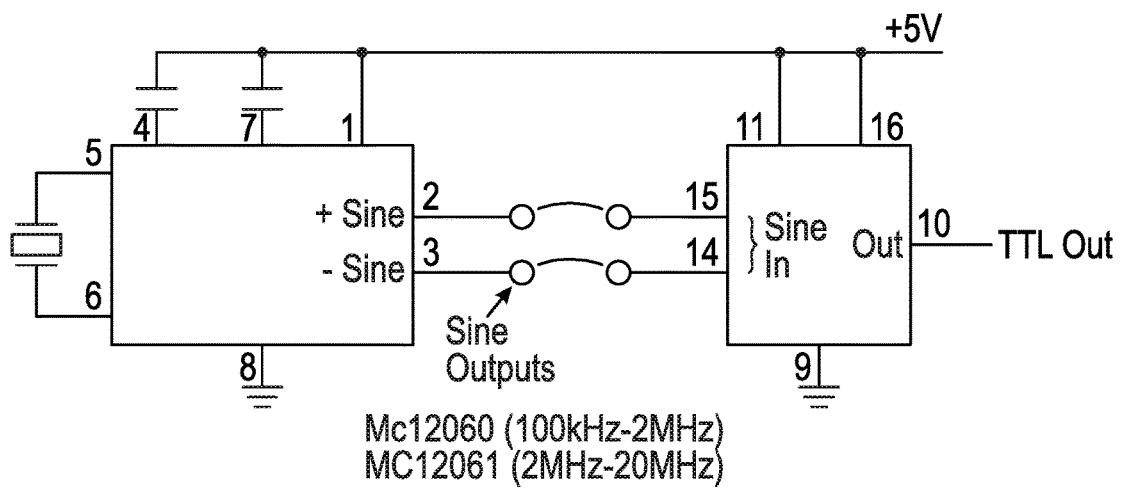

Specific circuits capable of producing acceptable oscillation are well known in the art. A representative sampling are shown in FIG. 3, which is taken from section 5.19 of the well known text: "The Art of Electronics $2^{nd}$ Edition", by Paul Horowitz and Winfield Hill, Cambridge University Press, 1989. Some circuits have even acquired names like the Pierce oscillator (FIG. 3A) and the Colpitts oscillator (FIG. 3B). Many others are within the skill of those in these arts. AT cut quartz crystals oscillating at frequencies from about 3 to 15 MHz are suitable, or from about 7 to 12 MHz, with about 9-10 MHz being most common.

Figure 4A:
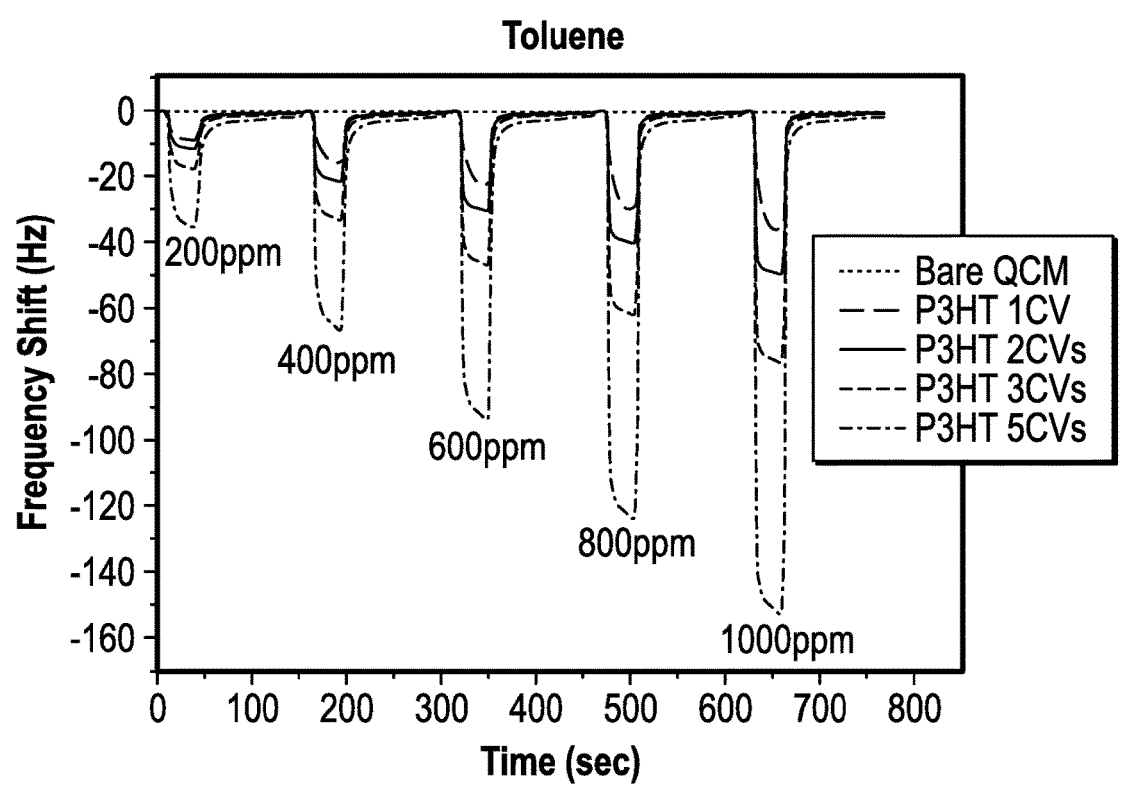
FIG. 4, in parts A, B and C, depict typical frequency response curves for QCM detectors of some known compounds.
Figure 4B:
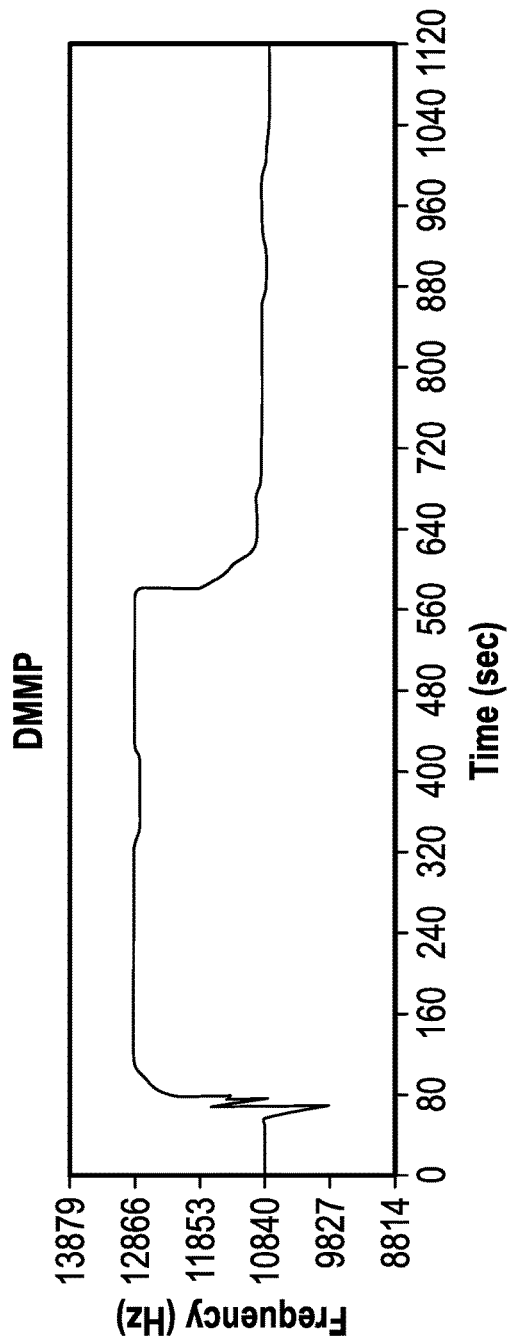
Figure 4B:
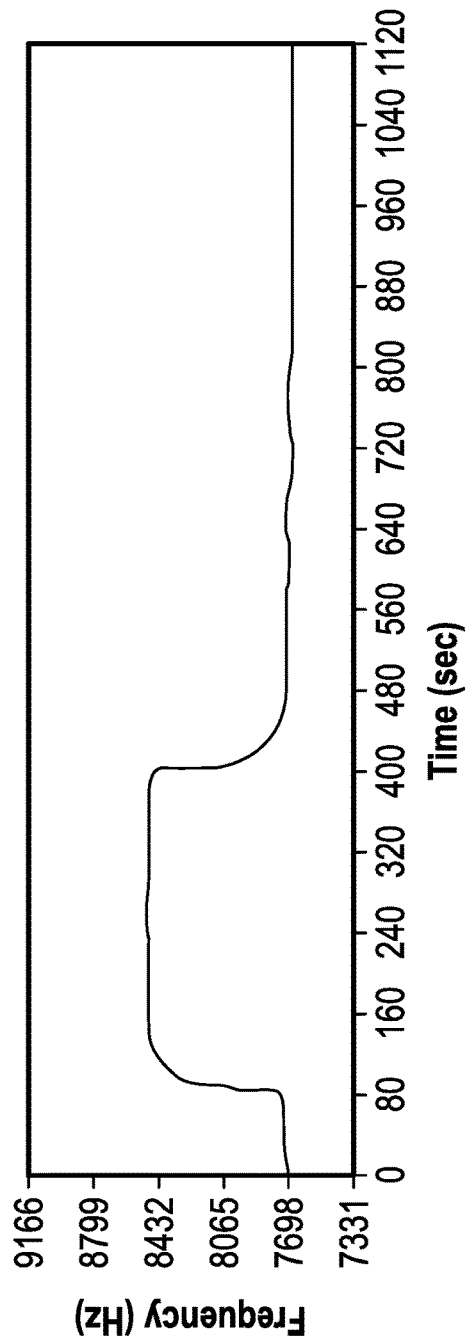
Figure 4C:
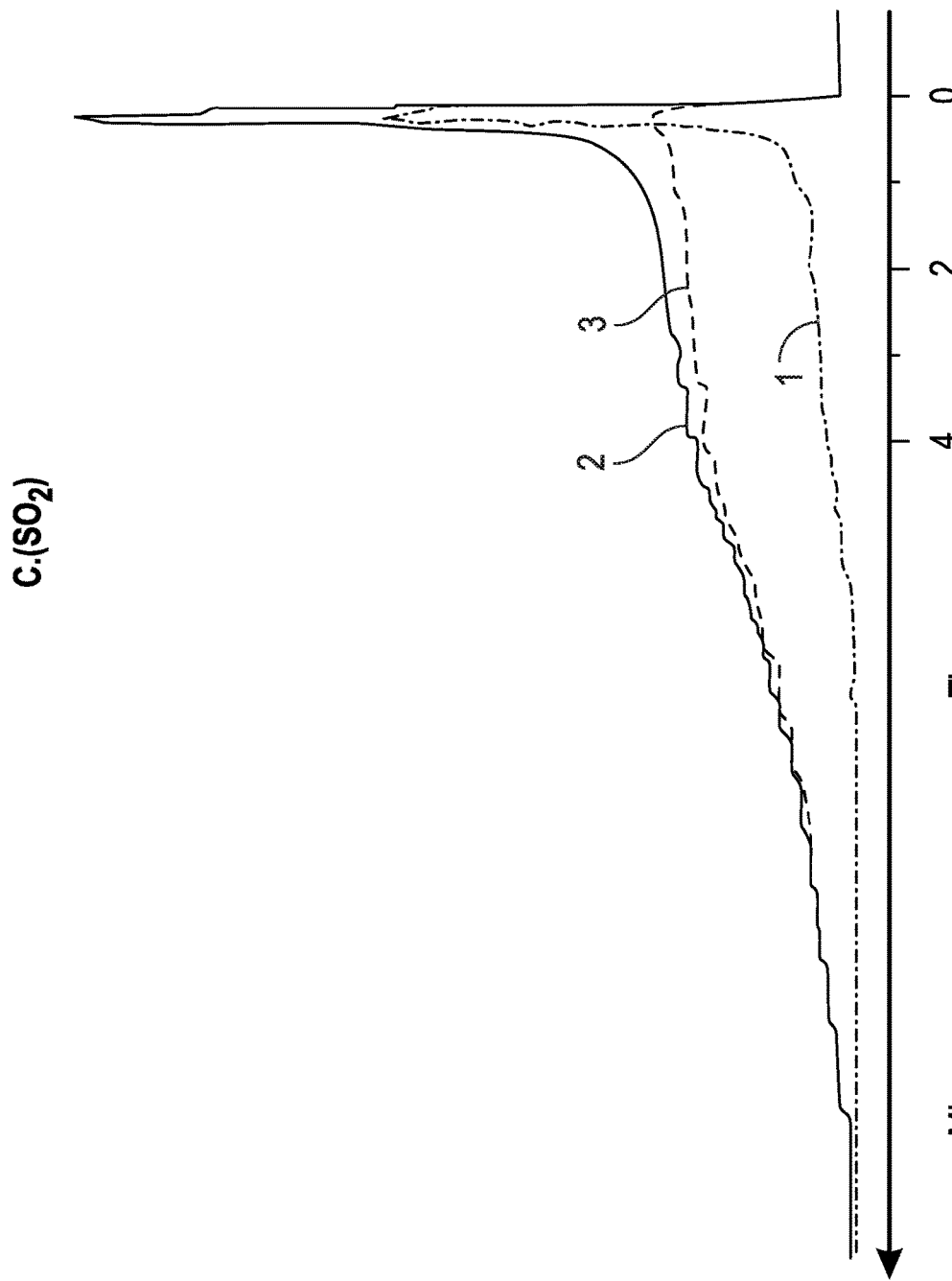

FIGS. 4A to 4C show the frequency response curves and the detectable frequency shifts that occur in the presence of a particular analyte. FIG. 4A shows the frequency shifts when concentrations of toluene ranging from 200 to 1000 ppm were detected on various thicknesses of a coating of poly(3-hexylthiophene) (p3HT). The coating films were made to increasing thicknesses by means of applying 1 to 5 scans of cyclic voltammetry. This work is described in more detail in *Polymer coated quartz crystal microbalance sensors for detection of volatile organic compounds in gas mixtures*, Si, et al. Analytica Chimica Acta, 597 (2007) 223-230, from which FIG. 4A is a representation of their FIG. 1. FIG. 4B shows the frequency shifts when a nerve gas stimulant, DMMP (Dimethyl Methylphosphonate), was detected over a period of time on 10 MHz crystals coated with proprietary polymers. This work is described in more detail in "*Polymer-Coated Piezoelectric Quartz Crystal Sensor for Sensing the Nerve Agent Simulant Dimethyl Methylphosphonate Vapor*," S. Maji, et al., J. Applied Polymer Science, February 2010, page 22, on which FIG. 4B is based. FIG. 4C shows the frequency shifts when sulfur dioxide ($SO_2$), was detected in the presence of water vapor (curve 2) and without water vapor (curve 3) on 9 MHz crystals. Curve (1) represents water vapor alone. This work is described in more detail in "*An Application of Artificial Neural Networks. Simultaneous Determination of the Concentration of Sulfur Dioxide and Relative Humidity with a Single Coated Piezoelectric Crystal*," W. Hongmei, et al., Anal. Chem. 1997, 69, 699-702, from which FIG. 4C is a representation of their FIG. 3.

Referring now to FIG. 1, an embodiment of a portable detection device 10 in accordance with the invention is illustrated in block diagram form. The device 10 includes a housing 12 into which are secured: a power source 14; one or more QCM sensors 16, 16' and associated oscillator circuits 18, 18'; a signal processing module 20; and an output 22. The housing has at least one opening 24, into which a QCM sensor 16 is fitted. Depending on the specific coating chemistry (discussed later) in some embodiments, the sensor 16 may be permanently installed and reusable; but in other embodiments the chemistry is irreversible and the sensor 16 is for "single use." In these latter types of embodiments, it is desirable to make the sensor 16 a "plug-in" module with terminal pins or contacts that electrically connect to the circuitry inside. In a variation, a second QCM sensor 16' may be employed. Typically the second sensor 16' is a reference sensor, which will be described in more detail later.

A powered oscillator circuit 18 coupled to the QCM sensor 16, 16' produces an alternating current between the electrodes of the QCM crystal, and sets up a standing shear wave in the crystal. In quartz AT cuts, the Q factor, which is the ratio of frequency and bandwidth, can be as high as $10^6$. Such a narrow resonance leads to highly stable oscillators and a high accuracy in the determination of the resonance frequency. Using a QCM sensor with these characteristics and properties provides great sensitivity and accuracy to the sensor of the device. Common equipment allows resolution down to 1 Hz or less on crystals with a fundamental resonant frequency in the 4-6 MHz range.

The standing wave frequency is detected by one of several possible frequency detection systems within the signal measurement and processing circuitry module 20, and a result is sent to the output 22. The output 22 is typically a visible display, such as an LED or LCD screen, but may alternatively or in addition include an audible or other detectable output. Power source 14 also supplies power for the signal measurement and processing module 20 and for the output 22 as needed. Power source may be any type of battery or current generator.

Note that when a second QCM sensor 16' is present, it will have its own oscillator circuit 18', the "prime" designation and dashed lines indicating an optional feature. Depending on the desired signal processing steps, there may be two separate frequency counter circuits 26, or there may be a "beat frequency" circuit 28 that compares two frequencies directly and generates a third, differential frequency that may be counted more easily, more quickly or more inexpensively. This "beat frequency" concept is alternatively known as heterodyning. The invention further contemplates that three or even more QCM sensors may be employed depending on design characteristics of the system. When more QCM sensors are employed, each will have its own oscillator circuit, but signal processing may combine and/or compare frequency signals, and may convert any of them to digital or other analog signals, such as for example a voltage that correlates to frequency. If two or more QCM sensors are employed usually at least one is a reference or control sensor. Reference sensors may contain no coating, and thereby control for environmental variables such as temperature that can cause frequency drift in the QCM sensors; or they may contain a coating without a capture reagent (described below) and thereby control for coating variability; or they may respond only to a known potentially interfering substance, in each case resulting in improved specificity accuracy. In three sensor systems, both types of controls may be employed, and an interference resolution module may become part of the signal processing module. Using suitable reference sensors ensures that many unwanted errors can be nulled out with the signal processing circuitry.

Frequency counters 26 are also well known electronic components and need little description here. Synchronous, asynchronous, ring, flip-flop, shift registers, etc. are all examples of counting devices. Portability is important so smaller devices are preferred. An exemplary free-standing counter, the IBQ2006ST is commercially available, as are counters manufactured by Yaesu, of Japan. However, it is to be understood that a suitable frequency counter circuit would likely be included within the same housing 12.

The signal measurement and processing module 20 may optionally be configured with a timing element to detect the change in frequency over time. Also, the frequency counters 26 and/or the beat frequency generator 28 may be configured to analyze the frequency at a first point in time, and again at a second point in time after exposure to the hydrocarbon gas with odorant. The before and after frequency values may be stored for further manipulation, such as a comparator function or differential analysis. Similarly, beat frequency counts may analyzed and or stored for pre- and post-exposure time points.

The odorant sensor device must be initially calibrated using at least two, and preferably three, accurately known concentrations of ethanethiol for testing the meter at low, medium, and full-scale readings; for example, 3 ppm, 5 ppm, and 10 ppm respectively. After this initial calibration, sensors can be manufactured with substantially the same sensitivity.

QCM Coatings

Ideally the QCM sensor is not only sensitive, but also specific for the analyte of interest, meaning it does not react to any appreciable extent to the other components of the reaction mixture, including impurities. In particular, oleophilic polymer coatings should be avoided as they would be expected to react significantly with the hydrocarbons in the gas and therefore be less specific. Thus, many hydrocarbon polymers and films must be avoided. The coating for the odorant sensor must be a material that either exhibits a specific absorptive attraction for the odorant—which may or may not be reversible—or undergoes a chemical reaction with the odorant—which typically is irreversible. In either case, the accumulation of mass captured by the coating on the crystal detectably alters its oscillation frequency, and this can be correlated as shown by Sauerbrey.

In general, the coatings may be oleophobic. Merriam-Webster defines oleophobic as "having or relating to a lack of strong affinity for oils." While various other definitions have been proposed for oleophobicity, they generally all relate to the extent to which the compound tends to avoid oil-like hydrocarbons. As used herein, an "oleophobic" coating is one in which the solubility of hydrocarbons is negligible; meaning that the solubility of hydrocarbons in the coating is not more than 6%—preferably less than 4%—of the solubility of the thiol-odorant in the in same coating.

In some embodiments, the coating may require no specific capture reagent and may merely adsorb the thiol odorant. However, in other embodiments, the coating may include a specific reagent for capturing or binding the thiol odorant. As previously noted, the "capturing" may be reversible or irreversible, and may occur by any of several mechanisms, including but not limited to adsorption, chelation, coordination complexes, or bond formation, such as a covalent bond.

A number of oleophobic coating reagents have been identified that are specific for thiol odorants in the hydrocarbon environment of natural gas. Some are reviewed by Knight and Verma in *Measurement of Odorant Levels in Natural Gas*, Arthur R. Knight and Arun Verma, Ind. Eng. Chem. Prod. Res. Dev. Vol. 15, No. 1, 1976, incorporated by reference. These include:

(a) Bis(p-nitrophenyldisulphide) in a phosphate buffer at pH 8 was shown to bind mercaptans, although the resulting color intensity effect was not found to be reliably concentration dependant.

(b) Mercury perchlorate with pyridine in an aqueous acetone solution caused formation of a white precipitate although no blue color as had been reported.

(c) Sodium nitrate and glacial acetic acid in aqueous solution reacted with mercaptans to produce a green color in solution, but bubbling of natural gas through the solution was found not to produce the color, probably due to insufficient contact time for the reaction to occur.

(d) Sodium nitroprusside in aqueous NaOH produced a green color in the presence of mercaptans, although the resulting color intensity effect was not found to be reliably concentration dependant. Similarly, $NH_4OH$ as the base produced a linearly correlated reddish color, but not when gas was bubbled through the solution.

(e) Phosphomolybdic acid in aqueous NaOH reacted with mercaptans to produce a blue product but the product appeared to be somewhat unstable.

(f) N-Ethylmaleimide in 2-propanol was found to react with mercaptans to produce a red-pink product and the color intensity effect varied linearly with concentration of mercaptan. This effect was maintained on bubbling of an odorant-containing gas stream through the solution, but the results were not reproducible in the presence of even trace quantities of water.

It is observed that, many of the chemistries described by Knight and Verma and summarized above would be suitable for colorimetric determination of thiol odorants in hydrocarbon gases—which easily would contain traces of moisture. However, applicant's invention does not rely on a colorimetric effect. Therefore, they should function as suitable coating reagents for the QCM sensors. They need not produce color, they only need to add mass to the sensor in order to alter the oscillation frequency.

Other reagent and coating systems have been described. For example, J. Hlavay and G. G. Guilbault, 1977, cited and incorporated previously, describe in Table I, a number of coating systems for detection of $SO_2$. Furthermore, they describe (p. 1894, first col.) a detection system for hydrogen sulfide [HSH] stating: "A method for selective detection of hydrogen sulfide in the atmosphere has been developed (33)[1]. This method is based on the adsorption of hydrogen sulfide on the surface of a quartz crystal coated by an acetone extract of various soots resulting from the burning of several organochlorine compounds. The extract of a soot prepared from chlorobenzoic acid provided the best substrate, and the method is most useful in the concentration range 1 to 60 ppm. [Paragraph] Other coating materials, such as lead acetate, metallic silver, metallic copper, and anthraquinone-disulfonic acid for detection of hydrogen sulfide with coated piezoelectric crystal were proposed by King (6)[2]."

[1] Hlavey Reference 33 is: L. M. Webber, K. H. Karmarkar, and G. G. Guilbault, Anal. Chem., in preparation.
[2] Hlavey Reference 6 is: W. H. King Jr, Anal. Chem., 36, 1735 (1964).

An alternative reagent coating system is described by Vashist and Vashist, 2011, cited previously, in which they write (page 3, first col.): "QCM-based sensor, with high sensitivity and quick response, was developed for the detection of methyl mercaptan ($CH_3SH$) by increasing the surface area of sensing polymeric film [6].[3] Poly(ethylene imine) (PEI) was used as polymeric layer, whereas $Al_2O_3$ porous film was used to increase the surface area by coating it using the sol-gel method on the QCM substrate between the QCM electrode and the polymeric film. The developed sensor detected 100 ppb of $CH_3SH$ gas and had interference with moisture, which can be corrected by using humidity sensor as feedback source."

[3] Vashist Reference 6 is: M. Kikuchi and S, Shiratori, "Quartz crystal microbalance (QCM) sensor for $CH_3SH$ gas by using polyelectrolyte-coated sol-gel film," Sensors and Actuators B, vol. 108, no. 1-2, pp 564-571, 2005.

Also, in doing the K-ratio work mentioned above (See *Vapor-Liquid Equilibrium Data for Ethyl Mercaptan in Propane Vapors*, R. W. Hankinson, Grant M. Wilson, Proceedings of the Fifty-Third Annual Convention, 1974, page 98), the authors wrote at page 99: "Considerable difficulty was encountered in obtaining reliable analyses for this project because the ethyl mercaptan appears to react with metal surfaces in sample lines, valves, analytical equipment, etc. This was particularly a problem because at the low concentrations of mercaptan being analyzed any reaction would drastically reduce the concentration. The gas chromatographic method proved to be totally unsatisfactory for this reason. However, we were able to develop a method for this project which appears to be quite reliable. The method depends on the quantitative reaction of ethyl mercaptan with silver nitrate to form the mercaptide as follows: (5)[4]

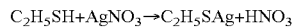

$$C_2H_5SH + AgNO_3 \rightarrow C_2H_5SAg + HNO_3$$

[4] Hankinson Reference 5 is: Reid, E. E. Organic Chemistry of Bivalent Sulfur, Vol. I, p 160, Chemical Publishing Co, New York, N.Y., (1958).

A dilute solution of silver nitrate in water was poured onto a 60-80 mesh support material obtained from natural weathered pumice. The resulting combination was then packed into short glass tubes of approximately 6 mm diameter by 6 inches in length. Individual analyses were then made by connecting a packed tube to either the vapor or liquid sample line after prior purging . . . ."

The coatings may be applied to the crystal using a variety of techniques, including direct application by painting, spraying, dipping, brushing, swapping, and any other method which transfers the coating from a supply solution to the crystal surface, with or without the evaporation of a solvent. Fortunately, each of the reagents described above is prepared in an aqueous, alcoholic or acetone formulation (all polar solvents). These might be applied and the solvent evaporated by drying or baking.

It is reiterated that all references cited herein, including books, journal articles, published U.S. or foreign patent applications, issued U.S. or foreign patents, and any other references, are each incorporated by reference in their entireties, including all data, tables, figures, and text presented in the cited references.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A portable device for detecting thiol odorants in a hydrocarbon gas, the device comprising:
   a housing;
   at least one piezo-crystalline substrate disposed in the housing and located for fluid communication with the hydrocarbon gas,
   a coating on the piezo-crystalline substrate, the coating capable of reacting specifically with and capturing thiol components from a gaseous phase, while substantially not reacting with the hydrocarbon gas itself;
   a power source;
   an oscillator circuit, the piezo-crystalline substrate forming a part of the oscillator circuit, whereby, when powered by the power source, the piezo-crystalline substrate oscillates at a first frequency prior being exposed to thiol odorants in a gas, and at a second frequency after being exposed to thiol odorants in the gas and capturing thiols in the coating, the second frequency differing from the first frequency in proportion to the amount of thiol captured.

2. The invention of claim 1 wherein the piezo-crystalline substrate is a quartz crystal.

3. The invention of claim 1 wherein the coating is applied directly to the surface of the crystal.

4. The invention of claim 1, further comprising a porous layer between the crystal and the coating to increase the surface area of the coating.

5. The invention of claim 1, further comprising at least one reference piezo-crystalline substrate disposed in the housing and located for fluid communication with the hydrocarbon gas.

6. The invention of claim 5, wherein the reference piezo-crystalline substrate is uncoated.

7. The invention of claim 1 wherein the coating is an oleophobic coating.

8. The invention of claim 7 wherein the coating comprises a reagent that substantially does not react with hydrocarbon vapors.

9. The invention of claim 1 wherein the coating comprises a reagent selected from the group consisting of:
   (a) Bis(p-nitrophenyldisulphide) in a phosphate buffer;
   (b) Mercury perchlorate with pyridine in an aqueous acetone solution;
   (c) Sodium nitrate and glacial acetic acid in aqueous solution;
   (d) Sodium nitroprusside in aqueous hydroxide base;
   (e) Phosphomolybdic acid in aqueous NaOH; and
   (f) N-Ethylmaleimide in 2-alcohol.

10. A method for detecting thiol odorants in a hydrocarbon gas using the hand-held portable detector of claim 1, the method comprising:
   providing a piezo-crystalline substrate having a coating capable of reacting specifically with and capturing thiol components from a gaseous phase while substantially not reacting with hydrocarbons of the gas, the piezo-crystalline substrate forming a part of an oscillator circuit that oscillates at a first frequency of oscillation;
   exposing the coated, piezo-crystalline substrate to a gas suspected to contain a thiol odorant for a time sufficient to allow the coating to capture thiols if present in the gas;
   powering the oscillator circuit after exposure to the gas to attain a second frequency of oscillation;

determining the extent to which the second frequency differs from the first frequency as a measure of the thiol captured from the gas.

11. The invention of claim 10 wherein the piezo-crystalline substrate is a quartz crystal.

12. The invention of claim 10 wherein the gas is a hydrocarbon gas consisting essentially of $C_1$ to $C_5$ hydrocarbons.

13. The invention of claim 12 wherein the gas is propane.

14. The invention of claim 12 wherein the gas is natural gas.

15. The invention of claim 10 wherein the thiol odorant is ethanethiol.

16. The invention of claim 10 wherein the coating is an oleophobic coating.

17. The invention of claim 16 wherein the coating comprises a reagent that substantially does not react with hydrocarbon vapors.

18. The invention of claim 10 wherein the coating comprises a reagent selected from the group consisting of:
   (a) Bis(p-nitrophenyldisulphide) in a phosphate buffer;
   (b) Mercury perchlorate with pyridine in an aqueous acetone solution;
   (c) Sodium nitrate and glacial acetic acid in aqueous solution;
   (d) Sodium nitroprusside in aqueous hydroxide base;
   (e) Phosphomolybdic acid in aqueous NaOH; and
   (f) N-Ethylmaleimide in 2-alcohol.

* * * * *